US011123731B2

(12) United States Patent
Fang et al.

(10) Patent No.: US 11,123,731 B2
(45) Date of Patent: Sep. 21, 2021

(54) MICROFLUIDIC DETECTION CHIP, PREPARATION METHOD THEREOF, FIXING DEVICE AND CENTRIFUGAL DETECTION DEVICE

(71) Applicants: Shanghai Igenetec Diagnostics Co., Ltd., Shanghai (CN); Shanghai Superchip Biotechnology Co., Ltd., Shanghai (CN)

(72) Inventors: Xueen Fang, Shanghai (CN); Jing Wu, Shanghai (CN); Jianghong Qian, Shanghai (CN)

(73) Assignee: Shanghai Igenetec Diagnostics Co., Ltd., Shanghai (CN)

( * ) Notice: Subject to any disclaimer, the term of this patent is extended or adjusted under 35 U.S.C. 154(b) by 0 days.

(21) Appl. No.: 16/632,037

(22) PCT Filed: May 13, 2019

(86) PCT No.: PCT/CN2019/086574
§ 371 (c)(1),
(2) Date: Jan. 17, 2020

(87) PCT Pub. No.: WO2020/010913
PCT Pub. Date: Jan. 16, 2020

(65) Prior Publication Data
US 2021/0114019 A1    Apr. 22, 2021

(30) Foreign Application Priority Data
Jul. 12, 2018 (CN) .......................... 201810761056.7

(51) Int. Cl.
*B81B 1/00* (2006.01)
*B01L 3/00* (2006.01)
*B32B 3/30* (2006.01)
*B32B 27/08* (2006.01)
*B32B 38/10* (2006.01)

(52) U.S. Cl.
CPC ..... *B01L 3/50273* (2013.01); *B01L 3/502707* (2013.01); *B32B 3/30* (2013.01);
(Continued)

(58) Field of Classification Search
None
See application file for complete search history.

(56) References Cited

U.S. PATENT DOCUMENTS

2002/0187560 A1* 12/2002 Pezzuto ............... B01F 5/0471
436/180
2016/0167045 A1* 6/2016 Kulinsky ............. B01D 21/262
494/37

FOREIGN PATENT DOCUMENTS

CN 103055981 A 4/2013
CN 203663854 U 6/2014
(Continued)

OTHER PUBLICATIONS

First Action dated Aug. 28, 2018 for Chinese Patent Application No. 201810761056.7.
(Continued)

*Primary Examiner* — Paul S Hyun
(74) *Attorney, Agent, or Firm* — Womble Bond Dickinson (US) LLP; Daniel E. Ovanezian

(57) ABSTRACT

The disclosure provides a microfluidic detection chip, a preparation method thereof, a fixing device and a centrifugal detection device. The detection chip comprises overlapped three layers. The upper layer of the chip includes a sample loading area and vents; the lower layer of the chip includes a waste liquid tank area in which a slope structure or a groove is disposed; the intermediate layer of the chip is a double-sided adhesive layer on which sample flow channels are divided by an adhesive area and an adhesive-free area. The self-driving and short-time centrifugation combined microfluidic detection chip technology designed by the
(Continued)

present disclosure can solve inherent problems of traditional paper substrates, further improve sample utilization, detection speed and detection sensitivity in immunoassay, and the preparation and assembly of the chip are simple, has low requirement for the detection device, and can be conveniently applied to the clinical detection.

5 Claims, 7 Drawing Sheets

(52) U.S. Cl.
CPC ......... *B32B 27/08* (2013.01); *B01L 2200/028* (2013.01); *B01L 2200/0684* (2013.01); *B01L 2200/12* (2013.01); *B01L 2300/0887* (2013.01); *B01L 2400/0409* (2013.01); *B32B 38/10* (2013.01)

(56) References Cited

FOREIGN PATENT DOCUMENTS

| | | |
|---|---|---|
| CN | 204679514 U | 9/2015 |
| CN | 105259162 A | 1/2016 |
| CN | 106434302 A | 2/2017 |
| CN | 106807461 A | 6/2017 |
| CN | 107126753 A | 9/2017 |
| CN | 207036852 U | 9/2017 |
| CN | 206701297 U | 12/2017 |
| CN | 108414773 A | 8/2018 |
| CN | 208526658 U | 2/2019 |
| EP | 3296019 A1 | 3/2018 |
| KR | 1020080090667 A | 10/2008 |
| TW | 201248148 A | 12/2012 |

OTHER PUBLICATIONS

Second Action dated Sep. 17, 2018 for Chinese Patent Application No. 201810761056.7.

Decision to Grant dated Sep. 28, 2018 for Chinese Patent Application No. 201810761056.7.

Iran Thi Thuy et al., "High-throughput profiling of N-linked oligosaccharides in therapeutic antibodies using a microfluidic CD platform and MALDI-MS", Analytical and Bioanalytical Chemistry, Dec. 21, 2010, pp. 1601-1611, vol. 399, No. 4, Springer, Berlin, DE.

Javier Atencia, "A robust diffusion-based gradient generator for dynamic cell assays", Lab on Chip, The Royal Society of Chemistry, Jan. 1, 2012, pp. 309-316.

\* cited by examiner

MICROFLUIDIC DETECTION CHIP, PREPARATION METHOD THEREOF, FIXING DEVICE AND CENTRIFUGAL DETECTION DEVICE

This application is a U.S. national stage application of the PCT International Application No. PCT/CN2019/086574 filed on May 13, 2019, which claims the benefit of foreign priority of Chinese patent application No. 201810761056.7 filed on Jul. 12, 2018, the content of which is incorporated herein by reference.

TECHNICAL FIELD

The present disclosure pertains to the field of medical detection, and particularly relates to a microfluidic detection chip for immune index detection, and to a detection device using the same.

BACKGROUND

Since its inception, immunochromatography has undergone the development from colloidal gold qualitative detection and semi-quantification to fluorescent quantification. The main method is to use the combination of nitrocellulose membrane, glass fiber membrane and absorbent paper as a flow substrate, and to immobilize antibodies coated by different markers thereon for a double antibody sandwich or competitive reaction. Because of its convenient use, rapid detection, direct separation of whole blood using a filter membrane, and low requirements for manufacturing equipment and detection equipment, it is currently widely used in the field of POCT (Point-of-care Testing).

However, it is difficult for reagent strips prepared from the paper substrate to overcome their inherent defects, mainly from the influence of the paper substrate itself on the immune reaction. The nitrocellulose membrane has limited ability to immobilize the protein, and there are many manual assembly steps, and the like. Defects such as high precision and low sensitivity between intra-assay and inter-assay lead to problems in actual clinical tests. In particular, it is not suitable for some clinic detection items having high sensitivity requirements, such as procalcitonin (PCT), N-terminal pro-brain natriuretic peptide (NT-proBNP), and troponin I (cTnI).

The microfluidic detection chip developed in the 1990s refers to a scientific and technical system that processes and controls $10^{-9}$ to $10^{-8}$ liters of liquid using channels of tens to hundreds of micrometers, which has many advantages such as small volume, low reagent consumption, fast analysis speed, automatic analysis process, easy integration, and high throughput. The benefits of microfluidic detection chips for immunoassay are as follows: substrates such as PMMA and PS themselves have strong adsorption capacity for proteins, and then the liquid is led to flow under the capillary action of the flow channel or an applied driving force. As a result, it is possible to conveniently realize immunochromatography reaction. In combination with a detection device, it is possible to conveniently perform quantitative measurement of the substance to be tested in a sample.

Patent document 1 discloses a microfluidic chip for fluorescence immunity detection and a preparation method thereof. The chip comprises a chip substrate, microfluidic channels arranged on the substrate, the microfluidic channels comprising a sample dropping area, a whole-blood filtering area, an antibody-coating area, a reaction area, a detection area, a quality control area and a waste liquid collecting area, which are connected in sequence. An erythrocyte filtering membrane is provided in the whole-blood filtering area. At the time of detection, being driven by a centrifugal force, the whole blood sample goes through the filtering area to remove the erythrocyte, for the subsequent detection. According to this scheme, on the one hand, the separation by the whole-blood filtering membrane will cause detection interference and sample waste, and on the other hand, the sample is liable to remain in the serpentine tube-like reaction area, which has an adverse effect on the detection sensitivity. In addition, the preparation method of directly opening channels on the substrate has a high processing cost, and the liquid flow rate may be too fast by simply controlling the liquid by the centrifugal force, which is not conducive to the progress of the chromatography reaction.

Patent document 2 discloses a magnetic particulate chemiluminiscence microfluidic chip for quantitatively detecting brain natriuretic peptide (BNP) in whole blood, which is composed of a top adhesive tape, a chip substrate and a bottom adhesive tape. On the chip substrate, a filtering area, a magnetic particulate tagged BNP antibody coating area, a reaction area, a cleaning area, a detection area, a liquid release channel are connected sequentially. In this method, magnetic particles modified by the antibody are used, and the preparation method is relatively complicated. The microfluidic chip requires an electromagnet to drive the magnetic particle in the chip to move during the detection, which requires high complexity of the device. In addition, the filtering area contains a blood filtering membrane, and there are also problems such as detection interference and sample waste.

Patent document 3 discloses a full-automatic microfluidic chip fluorescence immunodetection system, comprising a chip card storage disk, a sample tube disk and a centrifugal reaction disk. The centrifugal reaction disk has one or more chip card slots, of which the size matches a chip detection card, and the chip detection card is sequentially arranged with a sample loading slot, a fluorescent probe slot, a reaction detecting slot, a waste liquid slot, and microchannels connecting the above slots. By this system, the requirements of full-automatic, multi-sample, high-throughput and fast detection can be fundamentally realized. However, the assembly of this system is relatively complicated, and the reliability and convenience in the process of clamping the chip detection card and fixing it to the chip card slot on the centrifugal reaction disk need to be improved.

Patent document 4 discloses an overlapped three-layer chip structure, wherein the second layer is a double-sided adhesive film on which a microstructure is etched. The operation is simple and the production efficiency is high. The disadvantage is that how to arrange the microstructure on the double-sided adhesive film is not specifically described, and no other microstructures are designed on the first layer and the third layer. The chip prepared by this method needs to cooperate with a micro pump, a micro valve and a special detection equipment, and is suitable for some scientific research fields, not suitable for clinical point-of-care detection of biological samples.

Patent document 1: CN106807461A
Patent document 2: CN105259162A
Patent document 3: CN207036852U
Patent document 4: CN203663854U

SUMMARY

Problem to be Solved by the Present Disclosure

In order to solve the inherent problems of some paper substrates and the above-mentioned problems in the prior art, by using the microfluidic technology to further improve the sample utilization rate, the detection speed and the detection sensitivity in immunodetection, the disclosure designs a self-driving and short-time centrifugation combined microfluidic detection chip for detecting immune index, and a preparation method thereof. The preparation and assembly of the chip are simple, the chip has a low requirement for the detection device, and the chip can be conveniently applied to the clinical point-of-care detection of biological samples.

The present disclosure also provides a fixing device based on the microfluidic detection chip to achieve stability and convenience of clamping and fixing a plurality of chips. Further, the disclosure also provides a centrifugal detection device based on the microfluidic detection chip.

Solution for Solving the Problem

In order to solve the above-mentioned problems, the inventors have researched hard to design a microfluidic detection chip. Specifically, the disclosure includes the following technical solutions.

[1] A microfluidic detection chip comprising overlapped three layers including an upper layer, an intermediate layer, and a lower layer, wherein the upper layer of the chip comprises a sample loading area and a vent, the lower layer of the chip is provided with a slope structure or a groove, the intermediate layer of the chip is a double-sided adhesive layer, and a sample flow channel is divided by an adhesive area and an adhesive-free area on the double-sided adhesive layer, the sample flow channel comprises a sample tank area, a flow channel detection area, and a waste liquid tank area, the sample tank area corresponding to the sample loading area of the upper layer of the chip, the waste liquid tank area covering at least the slope structure or the groove of the lower layer of the chip, and the flow channel detection area being arc-shaped.

[2] The microfluidic detection chip according to [1], the sample loading area is also provided with a slope structure of which the angle is 15° to 45°, and on which one or more cylindrical convex drainage points are distributed.

[3] The microfluidic detection chip according to [1] or [2], the lower layer of the chip further comprises a drainage groove corresponding to the sample loading area.

[4] The microfluidic detection chip according to any one of the technical solutions of [1] to [3], a material for the upper layer of the chip and the lower layer of the chip is one selected from the group consisting of polystyrene (PS), polydimethylsiloxane (PDMS), polymethyl methacrylate (PMMA), polyethylene terephthalate (PET), glass or polycarbonate (PC); preferably, the material for the upper layer of the chip and the lower layer of the chip is selected from the group consisting of polymethyl methacrylate (PMMA), polystyrene (PS), or polycarbonate (PC); the intermediate layer of the chip is a polyethylene terephthalate (PET) adhesive or a polymethyl methacrylate (PMMA) adhesive.

[5] The microfluidic detection chip according to any one of the technical solutions of [1] to [4], the groove corresponds to a lower half of the waste liquid tank area and has a depth of 1 to 2 mm.

[6] The microfluidic detection chip according to any one of the technical solutions of [1] to [5], the upper layer of the chip and the lower layer of the chip both have a thickness of 1.5 to 2.5 mm, and the intermediate layer of the chip has a thickness of 0.05 to 0.5 mm.

[7] A method for preparing the microfluidic detection chip according to any one of the technical solutions of [1] to [6], the method comprising:

1) etching the sample flow channel in the double-sided adhesive layer by laser;

2) tearing off a peeling layer on one side of the double-sided adhesive layer, and sticking the double-sided adhesive layer on the surface of the lower layer of the chip; and 3) spotting in the sample flow channel, after drying, sticking the upper layer of the chip, and pressing.

[8] A fixing device for a microfluidic detection chip, wherein the fixing device is configured to simultaneously fix a plurality of microfluidic detection chips according to any one of the technical solutions of [1] to [6], and comprises a central fixing disk and a rotating tray, the central fixing disk being positioned above the rotating tray, and the rotating tray being divided by the central fixing disk into a plurality of areas respectively matching the microfluidic detection chip according to any one of the technical solutions of [1] to [6] in shape;

the fixing device is configured to fix the plurality of microfluidic detection chips according to any one of the technical solutions of [1] to [6] on the rotating tray by using respective sides of the central fixing disk;

the rotating tray has a light source transmitting area which is concentric with a flow channel detection area of the microfluidic detection chips according to any one of the technical solutions of [1] to [6].

[9] The fixing device for a microfluidic detection chip according to [8], wherein the central fixing disk is provided with positioning slots, which are evenly disposed on the sides of the central fixing disk.

[10] A centrifugal detection device comprising:

a microfluidic module, comprising the microfluidic detection chip according to any one of the technical solutions of [1] to [6], a fixing module, comprising the fixing device according to [8] or [9];

a rotating module connected to the fixing device and configured to drive the fixing device to rotate; and a detection module configured to detect the flow channel detection area of the microfluidic detection chip through the light source transmitting area of the fixing device, and output a detection result.

Effects of the Invention

The disclosure provides a self-driving and short-time centrifugation combined microfluidic detection chip, which has the following advantages: 1) there is no whole blood filtration step, so interference and sample waste due to the separation by a whole blood filtration membrane are avoided, and the whole blood sample directly participates in the reaction, so the utilization efficiency of the sample is higher; 2) the combination of self-driving and short-time centrifugation can well control the flow rate of the fluid, facilitate the progress of the chromatographic reaction; the sample is driven to flow in the flow channel under capillary action and centrifugation, and residual liquid is centrifugally removed from the flow channel detection area; besides, a groove is arranged on the lower layer of the chip to collect the centrifugally removed waste liquid; this design reduces non-specific binding and detection background to a certain extent, and improves the detection sensitivity; 3) the channel surface can be designed to immobilize more fluorescent microspheres and antibodies, which improves the detection sensitivity; 4) the preparation and assembly of the chip are relatively simple, and microstructures are also arranged on the first and third layers at the same time when a microfluid channel is arranged on the double-sided adhesive layer, so that it is not necessary to cooperate with a micro pump and a micro valve, the requirement for the detection equipment is small, and it can be easily applied to immunology single-item or multi-item determination.

The fixing device of the microfluidic detection chip of the disclosure ensures that the chip does not deviate from the centrifugal state under the state of high-speed centrifugation by the limitation of the central fixing disc, and the design of the arc side fully considers the operability and comfort of the hand when taking the chip.

The centrifugal detection device based on the microfluidic detection chip is convenient to assemble, easy to operate, has high detection sensitivity, and is suitable for large, medium and small medical institutions, emergency departments, community hospitals, home detection and scientific research, etc.

Figure 1:
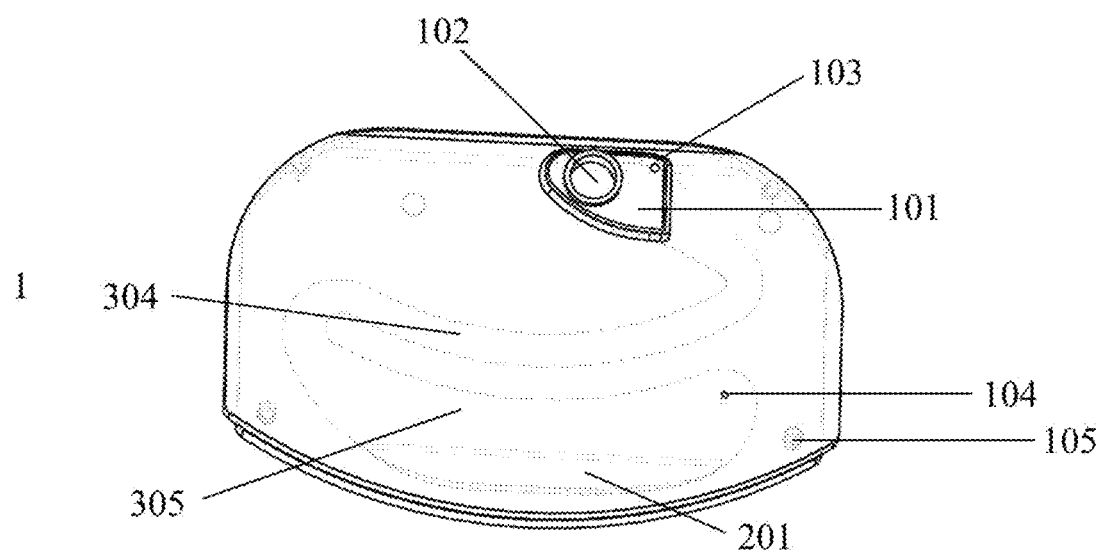
FIG. 1: an outline drawing of the first Example of the microfluidic detection chip provided by the disclosure.

DESCRIPTION OF THE REFERENCE NUMERALS microfluidic detection chip 1
upper layer of chip 100
lower layer of chip 200
intermediate layer of chip 300
sample loading area 101
sample loading hole 102
vent in sample loading area 103
vent in waste liquid tank area 104
column 105
drainage point 106
groove of lower layer of chip 201
column hole of lower layer of chip 202
slope structure of lower layer of chip 203
drainage groove 204
adhesive area 301
adhesive-free area 302
sample tank area 303
flow channel detection area 304
waste liquid tank area 305
column hole of intermediate layer 306
fixing device 2
centrifugal axis 3
fluorescent microsphere spotting area coated with antibodies 4
quality control antibody spotting area 5
detection antibody first spotting area 6
detection antibody second spotting area 7
slot 8
rotating tray 401
central fixing disk 402
stilt hole of rotating tray 403
light source transmitting area 404
positioning slot 405

DETAILED DESCRIPTION

In order to more clearly elaborate the above-mentioned object, features and advantages of the present disclosure, detailed embodiments of the present disclosure are described below in detail in combination with the drawings. Besides respective embodiments described here, the disclosure can also be implemented in other different manners. Persons skilled in the art can make corresponding improvements, modifications, and substitutions without departing from the spirit of the present disclosure. Thus, the disclosure is not limited by the detailed embodiments described here. The scope of protection of the disclosure should be determined based on the claims.

The term "comprising" or "comprises" and any variants thereof used in the description, claims and the above-mentioned drawings of the disclosure is intended to cover non-exclusive inclusion. For example, a process, method or system, product or apparatus comprising a series of steps or units is not limited to the listed steps or units but optionally may further comprise steps or units that are not listed, or optionally further comprises other steps or units inherent to said process, method, product or apparatus.

Besides, in order to elaborate the disclosure better, numerous specific details are set forth in the detailed embodiments below. Persons skilled in the art should understand that the <Microfluidic Detection Chip>

A microfluidic detection chip comprises overlapped three layers: an upper layer of the chip, a lower layer of the chip and an intermediate layer of the chip. The shape of the chip may be elliptical, square, rectangular, polygonal or circular, and preferably, the shape is elliptical to achieve better grip. The thickness of the upper and lower layers of the chip is 1.5 to 2.5 mm. If the thickness is too thin, the chip has too small sample loading amount and is liable to deform; if the thickness if too thick, the light transmittance will be affected, thereby affecting the detection result, and the thickness does not meet the needs of chip miniaturization. The thickness of the intermediate layer of the chip is 0.05 to 0.5 mm. The upper layer and the lower layer of the chip are adhered to each other by the intermediate layer or are fastened by adhesion of the intermediate layer in combination with snapping.

A material for the upper layer of the chip and the lower layer of the chip is one selected from the group consisting of polystyrene, polydimethylsiloxane, polymethyl methacrylate, polyethylene terephthalate, glass or polycarbonate; preferably, the material for the upper layer of the chip and the lower layer of the chip is selected from the group consisting of polymethyl methacrylate, polystyrene, or polycarbonate; the intermediate layer of the chip is a polyethylene terephthalate adhesive or a polymethyl methacrylate adhesive.

The upper layer of the chip is mainly used to lead a sample into a detection area. The upper layer of the chip comprises a sample loading area which is provided with a sample loading hole for loading a sample. The sample loading hole may be designed into a circle which closely matches a standard-sized pipette tip commonly used in biological experiments, and the diameter may be between 2 mm and 3 mm. The sample added through the sample loading hole can flow along the sample flow channel. Because the combination of gravity and capillary action self-driving and short-time centrifugation is used in the disclosure, it is unnecessary to fix a whole blood filtration device such as a whole blood filter membrane in the sample loading area of the disclosure, which can reduce sample waste and improve sample utilization efficiency. The shape of the sample loading area corresponds to the shape of the sample tank area of the intermediate layer of the chip. In a possible embodiment, the sample loading area is an irregular sector. In another possible embodiment, the sample loading area has a slope structure with an angle of 15° to 45°, and several cylindrical convex drainage points are distributed in the sample loading area. The drainage points have a diameter of 0.2 to 0.6 mm, a height of 0.2 to 0.6 mm, and an interval of 1 to 5 mm, and act to store the sample and drain the same.

The upper layer of the chip further comprises vents, namely, a vent in the sample loading area and a vent in the waste liquid tank area. The vents are through holes communicating with the atmosphere, preferably circular through holes to improve the fluidity of the sample solution, and the diameter may be in the range of 0.5 to 2.0 mm. In a possible embodiment, the upper layer is provided with one vent in the sample loading area and one vent in the waste liquid tank area. In another possible embodiment, a plurality of vents may be arranged in the sample loading area, depending on the number of the sample loading area.

In order to facilitate the assembly and fixing of the chip, the upper layer of the chip is provided with columns, and the number of the columns may generally be 2 to 4 set according to the actual needs. 4 columns are further preferably provided for the sake of better adaptation of the assembly.

The lower layer of the chip is provided with a slope structure or a groove that can be used to guide and store the waste liquid. In a possible embodiment, the slope structure has an angle of 15° to 45°, and several cylindrical convex drainage points are distributed in the slope structure. The drainage points have a diameter of 0.2 to 0.6 mm, a height of 0.2 to 0.6 mm, and an interval of 1 to 5 mm. The number of the drainage points is 3 to 10. In another possible embodiment, the lower layer of the chip is provided with a groove for collecting a residual waste liquid thrown away from a flow channel detection area during centrifugation. The groove corresponds to the lower half of the waste liquid tank area in the intermediate layer of the chip, and is shaped and has a depth of 1 to 2 mm. In other possible embodiments, the lower layer of the chip further comprises a drainage groove provided at a position corresponding to the sample application area in the upper layer of the chip. The drainage groove is a channel having a width of 0.2 to 0.6 mm and a depth of 0.1 to 0.5 mm, so as to guide the sample into the flow channel detection area. Besides, the lower layer of the chip may further comprise a certain number of column holes corresponding to the columns in the upper layer of the chip so as to reinforce the adaptation of the three layers of the chip.

The intermediate layer of the chip is a double-sided adhesive layer, and a sample flow channel is divided by an adhesive area and an adhesive-free area on the double-sided adhesive layer. The sample flow channel comprises is sample tank area, a flow channel detection area, and a waste liquid tank area, wherein the sample tank area corresponds to the sample loading area of the upper layer of the chip, and the shape of the sample tank area may be the same as that of the sample loading area of the upper layer of the chip. After the upper and lower layers of the chip are closely adhered to the intermediate layer of the chip, the waste liquid tank area mainly acts to store the waste liquid, that is, it is equivalent to a waste liquid tank. The shape of the waste liquid tank area at least completely covers the slope structure or groove of the lower layer of the chip. The waste liquid tank area may be the same as or larger than the size of the slope structure or the groove of the lower layer of the chip. The flow channel detection area is arc-shaped and has a bending radius of 25 to 35 mm (a radius centered on the centrifugal axis of the rotating tray of the fixed device), a radian in the range of 1.8 to 2.2 rad, and a width of 2 to 4 mm. The detection of immunological indicators is performed by immobilizing fluorescent microsphere-antibody markers and antibodies on the surface of the sample flow channel, and the detection sensitivity can be further increased by increasing the number of fluorescent microsphere-antibody markers and antibodies. The intermediate layer of the chip may further comprise a certain number of column holes corresponding to the columns on the upper layer of the chip, to fasten the adaptation of the three layers of the chip.

<Method of Preparing the Microfluidic Detection Chip>

The method of preparing the microfluidic detection chip of the present disclosure comprises:

1) etching the sample flow channel in the double-sided adhesive layer by laser;

Specifically, the double-sided adhesive layer may be etched by a laser engraving machine. In general, a microfluidic detection chip uses a lithography machine to etch a channel structure on a chip layer such as PDMS or PMMA. The lithography machine is expensive, and light source pollution exists during the lithography process. In the present disclosure, a channel structure is etched on the double-sided adhesive layer, which can improve production efficiency, reduce production cost, and reduce environmental pollution during the preparation.

2) tearing off a peeling layer on one side of the double-sided adhesive layer, and sticking the double-sided adhesive layer on the surface of the lower layer of the chip;

3) spotting in the sample flow channel, after drying, sticking the same to the upper layer of the chip, and pressing.

Specifically, a fluorescent microsphere spotting area coated with an antibody is disposed at a junction position of the flow channel detection area and the sample tank area, and a detection antibody second spotting area, a detection antibody first spotting area, and a quality control antibody spotting area are sequentially disposed along the direction of the sample flow. A quality control antibody spotting area is disposed to reduce intra-assay and/or inter-assay variation of the product and improve the product quality. Corresponding antibodies and fluorescent microsphere-antibody markers are added to the above-mentioned spotting areas, dried at 35 to 40° C. for 3 to 6 hours, preferably 4 hours. The upper layer of the chip is adhered and pressed. Where columns are disposed in the upper layer of the chip, the columns in the upper layer of the chip are inserted into the column holes in the intermediate layer and the lower layer of the chip to fasten the layers by means of adhesion in combination with snapping.

<Use of the Microfluidic Detection Chip>

When the microfluidic detection chip of the present disclosure is used, 100 to 300 µl of fresh blood can be directly dropped into the sample loading hole, and the sample flows in the sample flow channel under the action of gravity and capillary, and first mixes with fluorescent microspheres coated with a capture antibody, and then reacts with a detection antibody and a polyclonal antibody to generate a fluorescent signal. In general, the reaction of the sample may end after 10 to 15 minutes from the time when the sample is added to the sample loading hole, and then the sample flows into the waste liquid tank. The microfluidic detection chip is placed on the detection device and fixed. In the present disclosure, a plurality of chips can be fixed on the same fixing device, a centrifugal force is applied for 1 to 3 minutes, and the rotation speed is in the range of 2000 to 6000 rpm, for purpose of shaking off the residual liquid from the flow channel detection area. After that, the fluorescence intensities in the spotting area for detecting the quality control antibody and in the spotting area for detecting the antibody are read, where the spotting areas are within the detection area. The content of the immune index in the sample can be calculated according to a fitted calibration curve prepared by the standards for detection.

<Fixing Device for the Microfluidic Detection Chip>

Since the microfluidic detection chip of the present disclosure needs to work under high-speed centrifugation, in order to solve the fastness problem of clamping and fixing of the microfluidic detection chip under the centrifugal force, the disclosure also designs a fixing device cooperating with the microfluidic detection chip of the disclosure.

The fixing device is configured to simultaneously fix a plurality of microfluidic detection chips according to the disclosure. And the fixing device comprises a central fixing disk and a rotating tray, the central fixing disk being positioned above the rotating tray, and the rotating tray being divided into a plurality of areas respectively matching the microfluidic detection chip according to the disclosure in shape. And the fixing device is configured to fix the plurality of microfluidic detection chips according to the disclosure on the rotating tray by using respective sides of the central fixing disk. The rotating tray has a light source transmitting area which is concentric with a flow channel detection area of the microfluidic detection chips according to the disclosure. In a possible embodiment, the light source transmitting area is arc-shaped. The central fixing disk and the rotating tray can be fixed by screws.

In order to enhance stability of the fixation, the central fixing disk of the disclosure is provided with positioning slots, which are evenly disposed on the sides of the central fixing disk. The microfluidic detection chip of the disclosure is provided with slots on the side thereof, which forms clamping structures with the positioning slots. In general, each microfluidic detection chip cooperates with two positioning slots to prevent circumferential movement of the microfluidic detection chip relative to the central fixing disk. As another alternative embodiment, if a recessed structure is designed on the side of the microfluidic detection chip, an elastic ball plunger may be disposed on the side of the central fixing disk to form an elastic limiting assembly with the corresponding recessed structure of the microfluidic detection chip. Generally, two elastic ball plungers may be disposed for each microfluidic detection chip.

In a possible embodiment of the disclosure, the fixing device can simultaneously fix three microfluidic detection chips according to the present disclosure. The central fixing disk has three arc sides, which each is provided with two positioning slots. The central fixing disk and the rotating tray are fixed by a peripheral buckle, and the central fixing disk is located above the rotating tray. The rotating tray is thus divided into three areas which are similar in shape to the microfluidic detecting chip. The microfluidic detection chip is fixed in these areas by forming a clamping structure with the positioning slots.

In a possible embodiment, because the microfluidic detection chip is a small thin plastic sheet, the two edges on the outer side of the rotating tray may be arranged in an arc shape to match the arc structures on both sides of the microfluidic detection chip. The operability and comfort of the human hand to take the chip are fully considered.

In another possible embodiment, if a stilt is arranged on the microfluidic detection chip, a stilt hole may be correspondingly arranged on the rotating tray, which is conducive to the fastness of the chip on the tray.

<Centrifugal Detection Device Based on the Microfluidic Detection Chip>

The disclosure further provides a centrifugal detection device based on the microfluidic detection chip according to the disclosure, the centrifugal detection device comprising:

a microfluidic module, comprising the microfluidic detection chip according to the disclosure, a fixing module, comprising the fixing device according to the disclosure to fix several microfluidic detection chips;

a rotating module connected to the fixing device and configured to drive the fixing device to rotate and realize high-speed centrifugation of microfluidic detection chip; in a possible embodiment, the rotating module comprises a stepping motor such as a high speed micro stepping motor; and a detection module configured to detect the flow channel detection area of the microfluidic detection chip through the light source transmitting area of the fixing device, and output a detection result.

In a possible embodiment, the detection module comprises:

a light emitting unit configured to emit a first light;

a light propagation unit configured to propagate the first light to the light source transmitting area; when the rotating module drives a flow channel reaction area of the microfluidic detection chip to be rotated above the light source transmitting area, and the first light illuminates a sample of the flow channel reaction area through the light source transmitting area, the light propagation unit propagates a second light emitted by the sample under excitation of the first light; and a detection unit configured to detect the second light and generate a first signal according to the second light, wherein the first signal is an electric signal for analyzing the sample, and the first signal is taken as a detection result.

In a possible embodiment, the centrifugal detection device further comprises a temperature control module and an analysis module. The temperature control module is used to control the temperature of the flow channel detection area. The analysis module is configured to receive the detection result, analyze the sample according to the detection result, and output an analysis result.

Through the cooperation of the respective modules, the centrifugal detection device of the present disclosure can realize the immunological single-item or multi-item measurement, and the precision and detection sensitivity are higher than the traditional paper substrate immunochromatography method. For example, for the detection of procalcitonin index, the paper substrate immunochromatography product usually has an analytical sensitivity of 0.2 ng/mL, while the same may reach 0.05 ng/mL according to the present method. The immunoassay reagent prepared by the present method has an intra-assay and inter-assay precision of <10%, while it is 15% to 20% according to the common methods.

The following Examples are described to further demonstrate the present disclosure but do not constitute a limitation to the present disclosure.

EXAMPLES

Example 1

This example provided a microfluidic detection chip for detecting the content of procalcitonin in whole blood.

FIG. 1 shows an outline drawing of the microfluidic detection chip of this example. From FIG. 1 to FIG. 4, it can be seen that the microfluidic detection chip 1 had an elliptical shape of which the maximum values of the length, width and height were 55 mm×35 mm×4 mm. The chip 1 comprised overlapped three layers: an upper layer 100 of the chip, a lower layer 200 of the chip, and an intermediate layer 300 of the chip.

Figure 2:
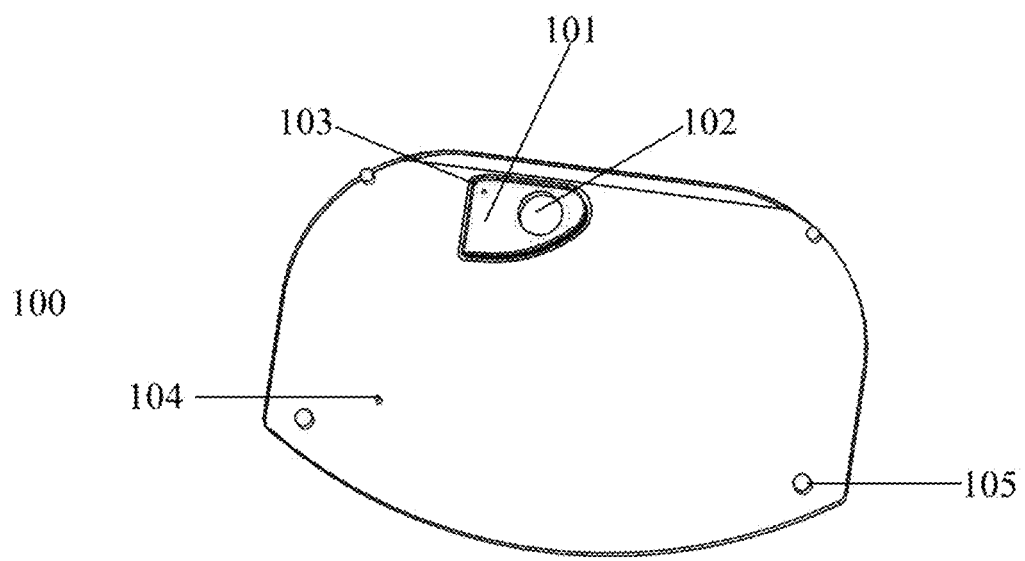
FIG. 2: a structure diagram of the upper layer in the first Example of the microfluidic detection chip provided by the disclosure.

The upper layer 100 of the chip was made of PMMA and had an elliptical shape, and the upper layer 100 had a thickness of 2.0 mm. FIG. 2 shows a structure of the upper layer 100 of the chip. It can be seen that the upper layer 100 of the chip comprised a sample loading area 101, which was provided with a sample loading hole 102 having a diameter of 4 mm, for adding a sample. The sample loading area 101 had a shape of an irregular sector. The upper layer 100 of the chip further comprised two vents, i.e., a vent 103 in the sample loading area and a vent 104 in the waste liquid tank as shown in FIG. 1. The vents were through holes communicating with the atmosphere, to improve the fluidity of the sample solution, and had a diameter of 1.0 mm.

To facilitate the assembly and fixation of the chip, the upper layer 100 of the chip was provided with four columns 105.

Figure 3:
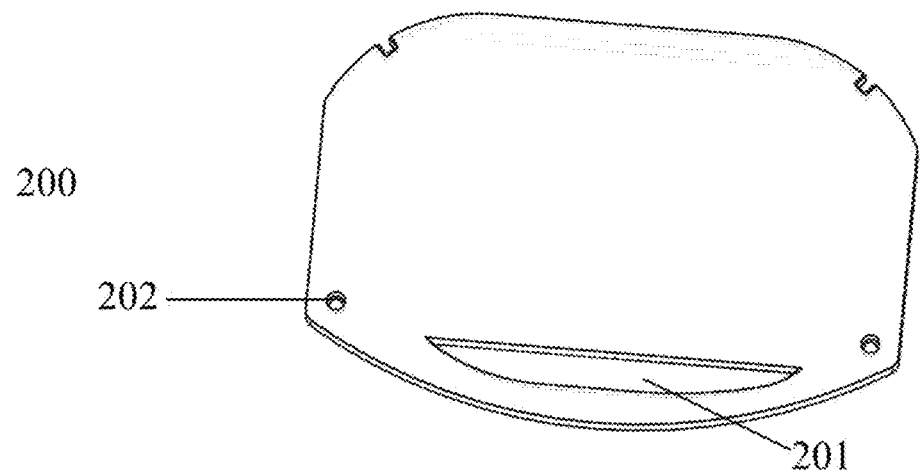
FIG. 3: a structure diagram of the lower layer in the first Example of the microfluidic detection chip provided by the disclosure.

The lower layer 200 of the chip was made of PMMA, had a shape matching the upper layer of the chip, and had a thickness of 2.0 mm. FIG. 3 shows a structure of the lower layer 200 of the chip, which comprised a groove 201 for collecting the residual waste liquid during centrifugation, and which was shaped, and the maximum values of the length, width and depth were 32 mm×3.3 mm×1.5 mm. The lower layer of the chip further comprised column holes 202 of the lower layer of the chip.

Figure 4:
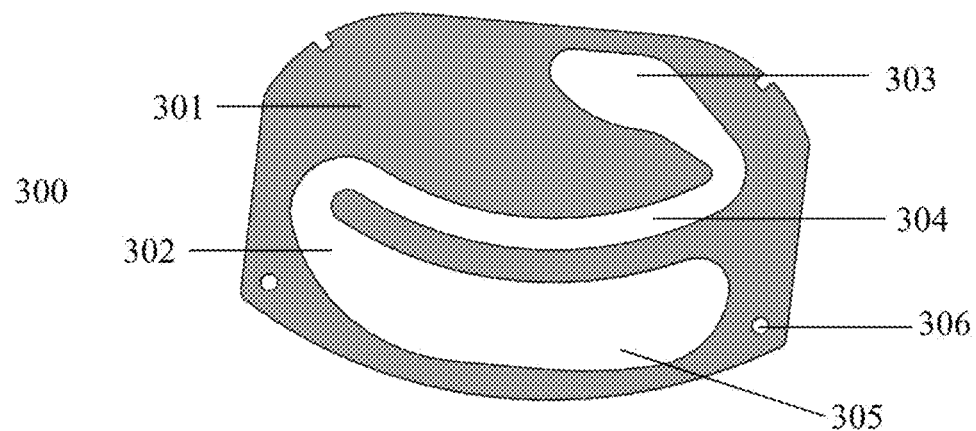
FIG. 4: a structure diagram of the intermediate layer in the first Example of the microfluidic detection chip provided by the disclosure.

The intermediate layer of the chip was a double-sided adhesive layer, which was made of PET, and had a thickness of 0.05 mm. FIG. 4 shows a structure of the intermediate layer 300 of the chip. A sample flow channel was divided by an adhesive area 301 (the dark area) and an adhesive-free area 302 (the light area) on the double-sided adhesive layer. And the sample flow channel comprised three areas: a sample tank area 303, a flow channel detection area 304, and a waste liquid tank area 305, wherein the sample tank area 303 had a shape completely the same as the sample loading area 101 of the upper layer of the chip, the waste liquid tank area 305 completely covered the groove 201 of the lower layer of the chip and had an area larger than that of the groove. The flow channel detection area had a width of 3 mm and a length of 30 mm. The flow channel detection area had a bending radius of 32 mm and a radian of 2.09 rad. The intermediate layer of the chip further comprised column holes 306 of the intermediate layer of the chip.

Figure 5:
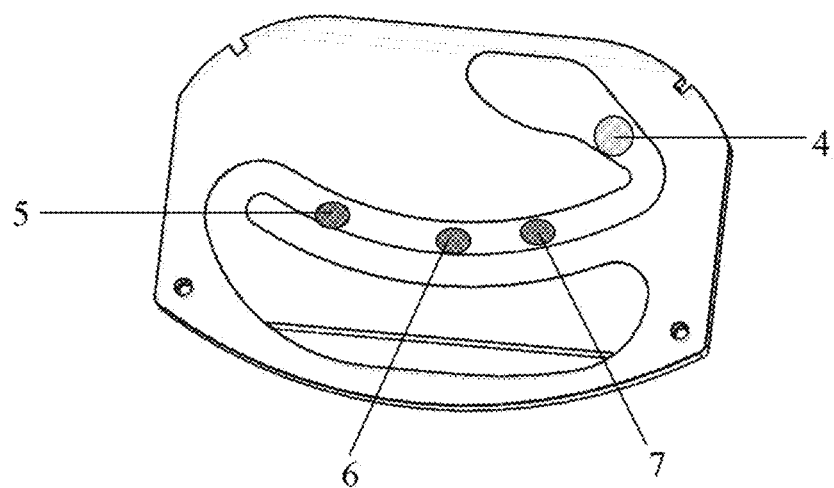
FIG. 5: a diagram of a reagent fixing area in the first Example of the microfluidic detection chip provided by the disclosure.

When the detection chip was prepared, an adhesive film on one side of the intermediate layer 300 of the chip was peeled off first, and then the intermediate layer 300 of the chip was adhered to the lower layer 200 of the chip. As shown by FIG. 5, 0.05 ng of goat anti-mouse polyclonal antibody was added to an exposed quality control antibody spotting area 5 in the sample flow channel, 0.02 ng of procalcitonin detection antibody was added to a detection antibody first spotting area 6, and 0.01% solid content fluorescent microspheres coated with 0.02 ng of procalcitonin capture antibody was added to a fluorescent microsphere spotting area 4 coated with antibodies. After drying at 37° C. for 4 hours, an upper layer cover of the chip was adhered and pressed.

Figure 6:
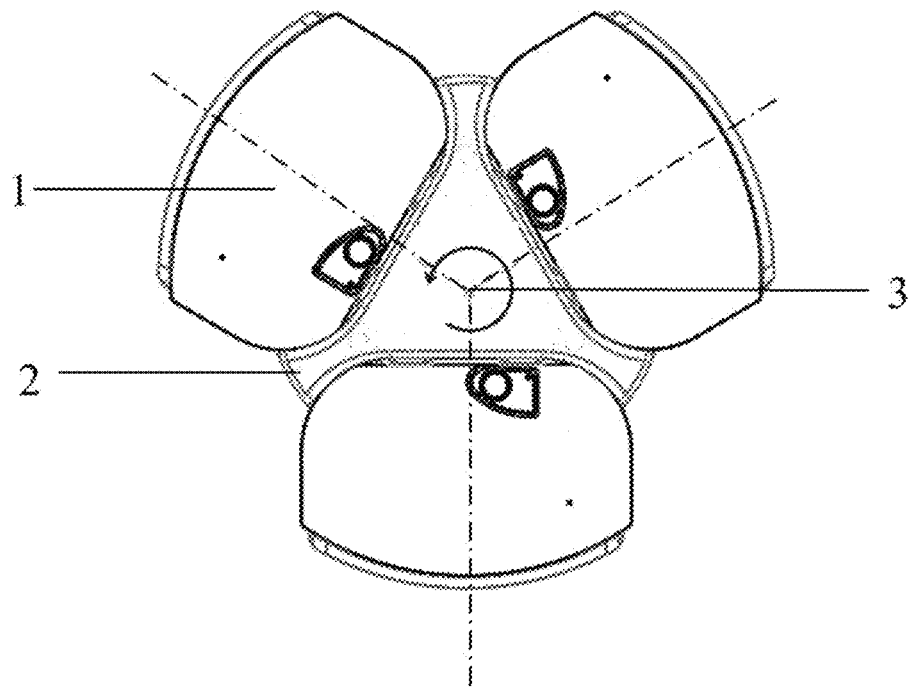
FIG. 6: a diagram showing that the first Example of the microfluidic detection chip provided by the disclosure is fixed to the fixing device of the disclosure and performs detection.

At the time of the detection, 100 μl of whole blood was directly added to the sample loading hole 102. After 10 minutes, the reaction of the sample ended, and the liquid all flowed into a waster liquid tank 201. The microfluidic detection chip 1 was placed on the fixing device. As shown in FIG. 6, three microfluidic detecting chips might be fixed on a fixing device 2, and a counterclockwise centrifugal force of 5000 rpm was applied for 1 minute around a centrifugal axis 3. Then, the fluorescence intensities in the spotting area for detecting the quality control antibody and in the spotting area for detecting the antibody are read, where the spotting areas are within the detection area. The procalcitonin content in the sample can be calculated according to a fitted calibration curve prepared by the standards for detection. To detect procalcitonin in whole blood by using this method, it took only 10 to 15 minutes from the loading of sample to reading the result, the analytical sensitivity could reach 0.05 ng/mL, and the detection range was 0.05 ng/mL to 100 ng/mL, which was close to the detection performance of chemiluminescence.

Example 2

This example provided a microfluidic detection chip of another structure, for detecting the content of procalcitonin in whole blood.

Figure 7:
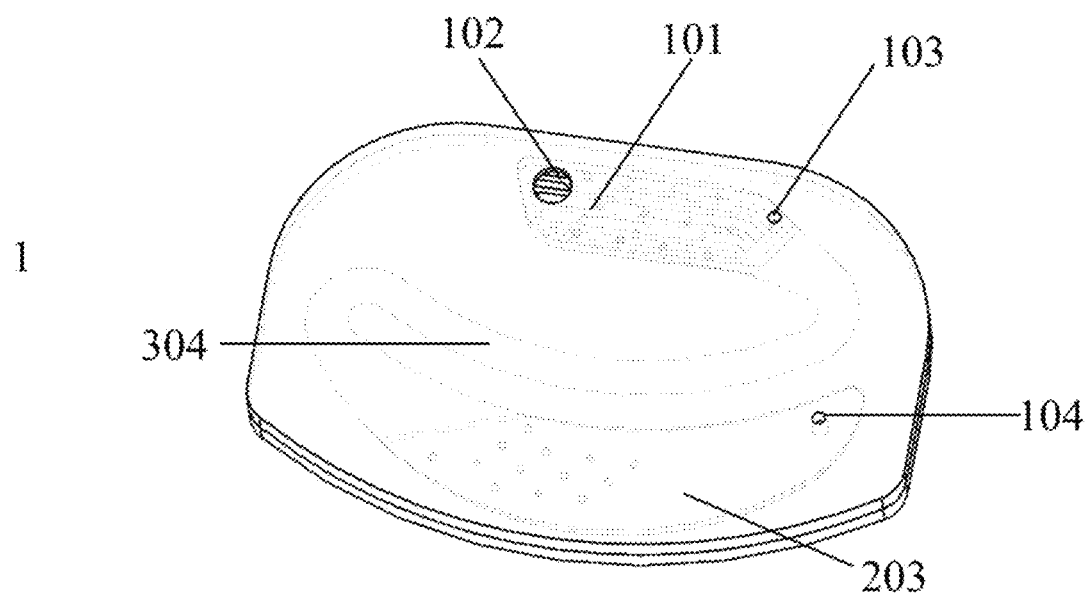
FIG. 7: an outline drawing of the second Example of the microfluidic detection chip provided by the disclosure.

FIG. 7 shows an outline drawing of the microfluidic detection chip of this example. From FIG. 7 to FIG. 10, it can be seen that the microfluidic detection chip 1 had an elliptical shape of which the maximum values of the length, width and height were 55 mm×35 mm×4 mm. The chip 1 comprised overlapped three layers: an upper layer 100 of the chip, a lower layer 200 of the chip, and an intermediate layer 300 of the chip.

Figure 8:
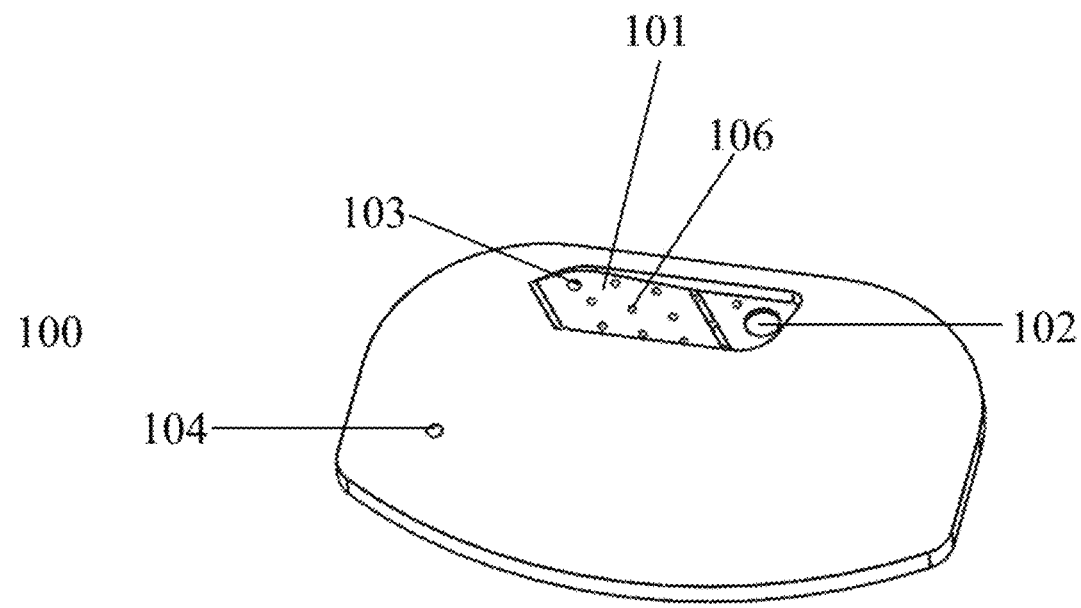
FIG. 8: a structure diagram of the upper layer in the second Example of the microfluidic detection chip provided by the disclosure.

The upper layer 100 of the chip was made of PMMA and had an elliptical shape, and the upper layer 100 had a thickness of 2.0 mm. FIG. 8 shows a structure of the upper layer 100 of the chip. It can be seen that the upper layer 100 of the chip comprised a sample loading area 101, which was provided with a sample loading hole 102 having a diameter of 3 mm, for adding a sample. The sample loading area 101 had a slop of 25°, on which several cylindrical convex drainage points 106 having a diameter of 0.4 mm, a height of 0.4 mm and an interval of 4 mm were distributed, for the drainage of the sample. The sample loading area 101 had a shape of an irregular sector. The upper layer 100 of the chip further comprised two vents, i.e., a vent 103 in the sample loading area and a vent 104 in the waste liquid tank as shown in FIG. 8. The vents were through holes communicating with the atmosphere, to improve the fluidity of the sample solution, and had a diameter of 1.0 mm.

Figure 9:
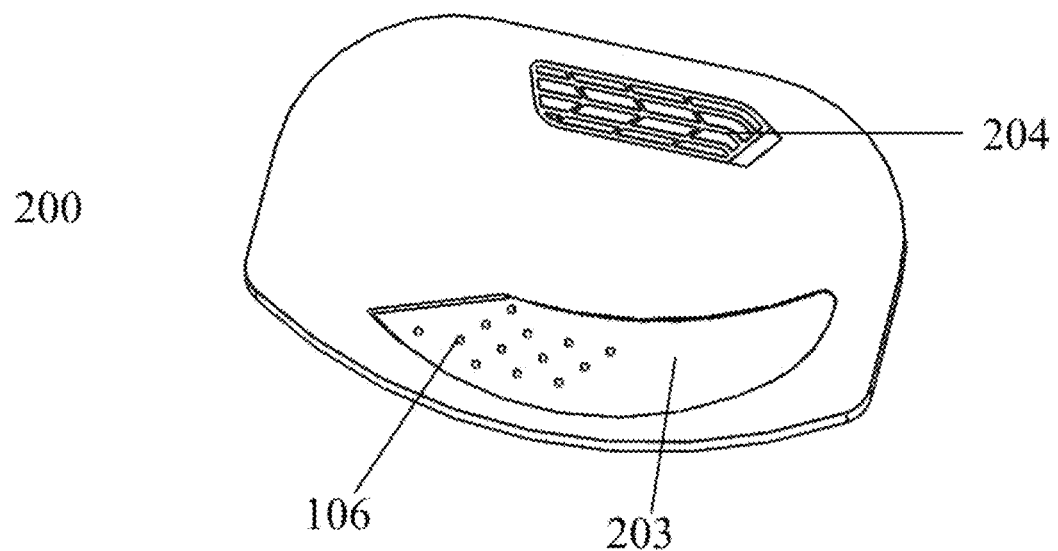
FIG. 9: a structure diagram of the lower layer in the second Example of the microfluidic detection chip provided by the disclosure.

The lower layer 200 of the chip was made of PMMA, had a shape matching the upper layer of the chip, and had a thickness of 2.0 mm. FIG. 9 shows a structure of the lower layer 200 of the chip, which comprised an irregular shaped slope structure 203 having an angle of 20°, and having a length of up to 41 mm and a width of up to 8 mm. Several cylindrical convex drainage points 106 having a diameter of 0.4 mm, a height of 0.4 mm and an interval of 4 mm were distributed on the slope structure 203, for the drainage of the sample. The lower layer 200 of the chip was provided with a drainage groove 204 at a position corresponding to the sample loading area 101 of the upper layer 100 of the chip. The width of the drainage groove had a width of 0.4 mm and a depth of 0.1 mm, for guiding the sample into the sample flow channel.

Figure 10:
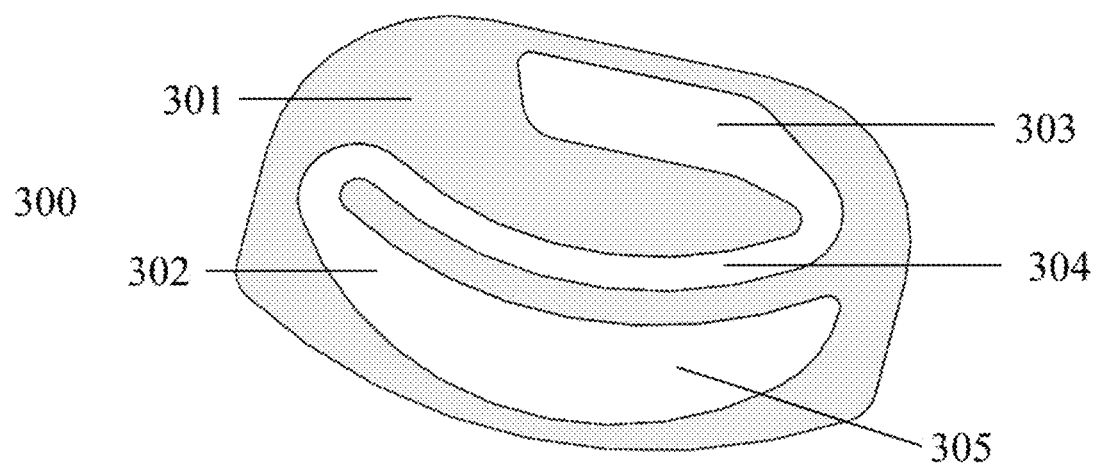
FIG. 10: a structure diagram of the intermediate layer in the second Example of the microfluidic detection chip provided by the disclosure.

The intermediate layer of the chip was a double-sided adhesive layer in which the upper layer of the chip and the lower layer of the chip were adhered to form a flow channel. The intermediate layer of the chip was made of PET and had a thickness of 0.05 mm. FIG. 10 shows a structure of the intermediate layer 300 of the chip, which was a double-sided adhesive layer. A sample flow channel was divided by an adhesive area 301 (the dark area) and an adhesive-free area 302 (the light area) on the double-sided adhesive layer. And the sample flow channel comprised a sample tank area 303, a flow channel detection area 304, and a waste liquid tank area 305, wherein the sample tank area 303 corresponded to the sample loading area 101 of the upper layer of the chip, the waste liquid tank area 305 corresponded to a slope structure 203 in the lower layer of the chip, and the waste liquid tank area 305 completely covered the slope structure 203 in the lower layer of the chip and had an area larger than that of the slope structure. The flow channel detection area had a width of 3 mm, and had a bending radius of 32 mm and a radian of 2.09 rad.

Figure 11:
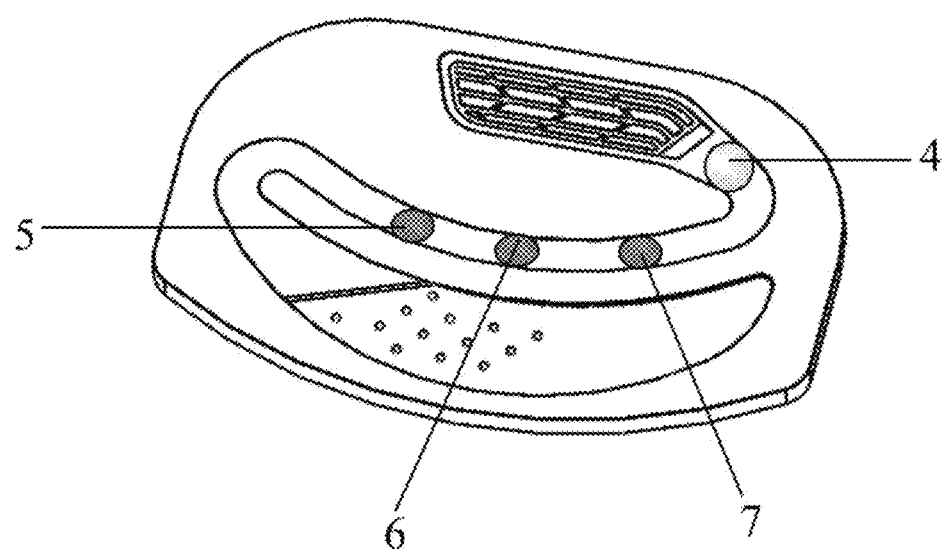
FIG. 11: a diagram of a reagent fixing area in the second or third Example of the microfluidic detection chip provided by the disclosure.

When the detection chip was prepared, an adhesive film on one side of the intermediate layer 300 of the chip was peeled off first, and then the intermediate layer 300 of the chip was adhered to the lower layer 200 of the chip. As shown by FIG. 11, 0.05 ng of goat anti-mouse polyclonal antibody was added to an exposed quality control antibody spotting area 5 in the sample flow channel, 0.02 ng of procalcitonin detection antibody was added to a detection antibody first spotting area 6, and 0.01% solid content fluorescent microspheres coated with 0.02 ng of procalcitonin capture antibody was added to a fluorescent microsphere spotting area 4 coated with antibodies. After drying at 37° C. for 4 hours, an upper layer cover of the chip was adhered and pressed.

Figure 12:
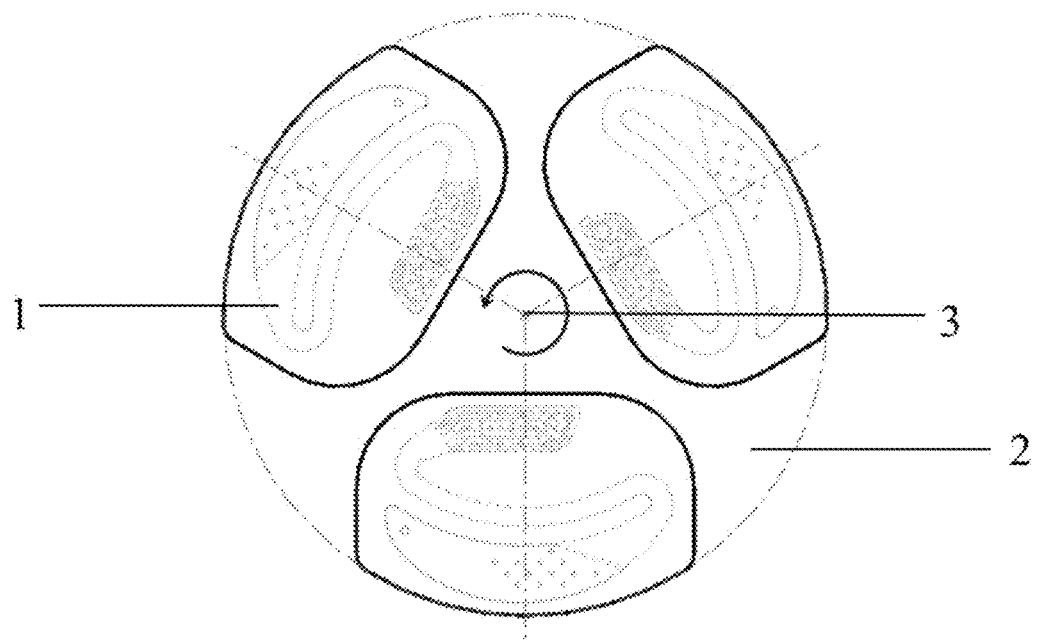
FIG. 12: a diagram showing that the second or third Example of the microfluidic detection chip provided by the disclosure is fixed to the fixing device of the disclosure and performs detection.

At the time of the detection, 100 μl of whole blood was directly added to the sample loading hole 102. After 10 minutes, the reaction of the sample ended, and the liquid all flowed into a waster liquid tank 201. The microfluidic detection chip 1 was placed on the fixing device. As shown in FIG. 12, three microfluidic detecting chips might be fixed on a fixing device 2, and a counterclockwise centrifugal force of 5000 rpm was applied for 1 minute around a centrifugal axis 3. Then, the fluorescence intensities in the spotting area for detecting the quality control antibody and in the spotting area for detecting the antibody are read, where the spotting areas are within the detection area. The procalcitonin content in the sample can be calculated according to a fitted calibration curve prepared by the standards for detection. The detected properties were the same as Example 1.

Example 3

In this example, the microfluidic detection chip had a structure the same as Example 2, for simultaneous detection of the content of procalcitonin and C-reactive protein in whole blood.

The preparation steps of the microfluidic detection chip were substantially the same as Example 2 except for the substances added to the sample spotting areas. As shown by FIG. 11, spotting was performed in the sample flow channels. Respectively, 0.05 ng of goat anti-mouse polyclonal antibody was added to a quality control antibody spotting area 5, 0.02 ng of procalcitonin detection antibody was added to a detection antibody first spotting area 6, 0.05 ng of C-reactive protein detection antibody was added to a detection antibody second spotting area 7, and a fluorescent antibody mixture was added to a fluorescent microsphere spotting area 4 coated with antibodies, specifically, a mixture of a 0.05% solid content fluorescent microsphere coated with 0.02 ng of procalcitonin capture antibody and a 0.05% solid content fluorescent microsphere coated with 0.05 ng of C-reactive protein capture antibody. After drying at 37° C. for 4 hours, an upper layer cover of the chip was adhered and pressed.

At the time of the detection, 120 μl of whole blood was directly added to the sample loading hole 102. After 15 minutes, the reaction of the sample ended, and the liquid all flowed into a waster liquid tank 201. The microfluidic detection chip 1 was placed on the fixing device. As shown in FIG. 12, three microfluidic detecting chips might be fixed on a fixing device 2, and a counterclockwise centrifugal force of 2000 rpm was applied for 2 minutes around a centrifugal axis 3. Then, the fluorescence intensities in the spotting area for detecting the quality control antibody and in the spotting area for detecting the antibody are read, where the spotting areas are within the detection area. The procalcitonin content and the C-reactive protein content in the sample can be calculated according to a fitted calibration curve prepared by the standards for detection. By using this method, the procalcitonin analytical sensitivity could reach 0.05 ng/mL, and the detection range was 0.05 ng/mL to 100 ng/mL; the C-reactive protein analytical sensitivity could reach 0.5 mg/L, and the detection range was 0.5 to 100 mg/L.

Example 4

This example provided a fixing device for a microfluidic detection chip, which was used for clamping and fixing the microfluidic detection chip described in Example 1.

Figure 13:
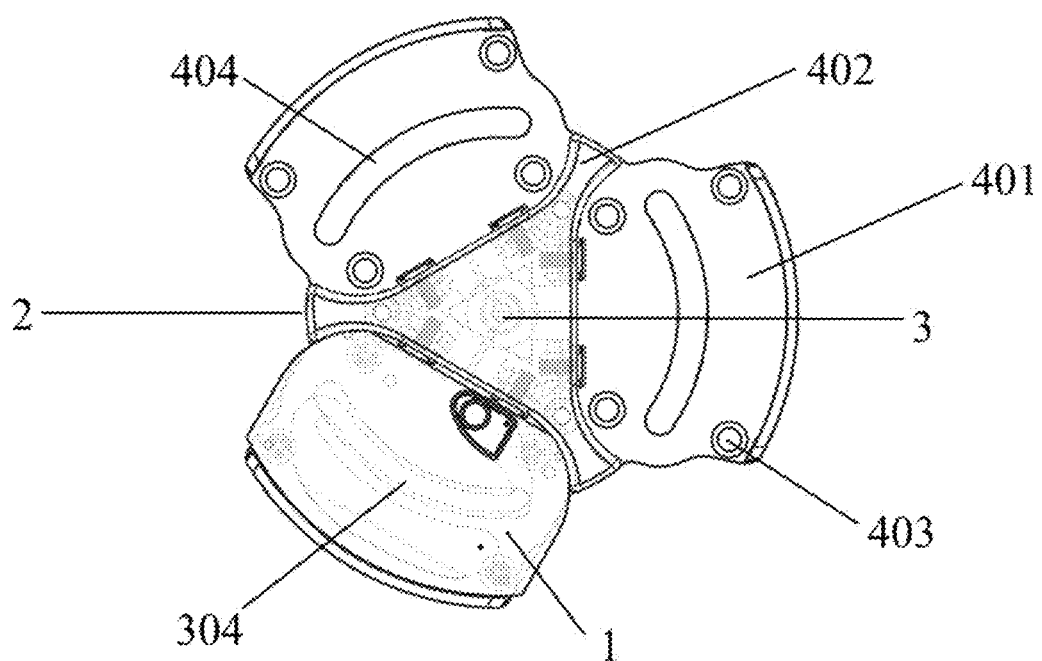
FIG. 13: a diagram showing assembly in the fourth Example of the fixing device of microfluidic detection chip provided by the disclosure.

As shown by FIG. 13, the fixing device 2 comprised a rotating tray 401 and a central fixing disk 402 which were concentric, and the axis of both the rotating tray 401 and the central fixing disk 402 was a centrifugal axis 3. The rotating tray 401 was divided by the central fixing disk 402 into three areas matching the microfluidic detection chip described in the disclosure in shape. In the rotating tray, there was a light source transmitting area 404 which was concentric with a flow channel detection area 304 of the microfluidic detection chips described in the disclosure, and which was an arc through hole. The rotating try 401 was provided with stilt holes 403 corresponding to the stilts in the lower layer of the microfluidic detection chips.

Figure 14:
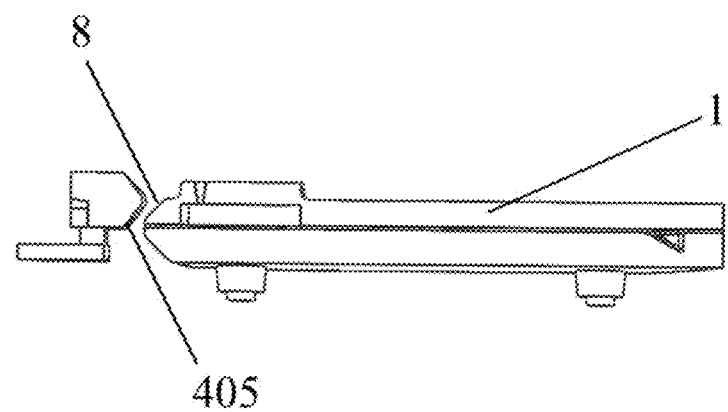
FIG. 14: a diagram showing positioning slot fitting in the fourth Example of the fixing device of microfluidic detection chip provided by the disclosure.

In order to reinforce the stability of the fixation, positioning slots 405 are evenly disposed on the sides of the central fixing disk 402. As shown by FIG. 14, a slot 8 is disposed on the sides of the microfluidic detection chip of the present disclosure, to form a clamping structure with the positioning slot 405. In general, each microfluidic detection chip cooperates with two positioning slots 405 to prevent circumferential movement of the microfluidic detection chip relative to the central fixing disk.

What is claimed is:

1. A microfluidic detection chip comprising overlapped three layers including an upper layer, an intermediate layer, and a lower layer, wherein
    the upper layer of the chip comprises a sample loading area and a vent,
    the lower layer of the chip is provided with a slope structure or a groove,
    the intermediate layer of the chip is a double-sided adhesive layer, and a sample flow channel is defined by a cutout of the intermediate layer such that a perimeter of the sample flow channel is bound by the double-sided adhesive layer,
    the sample flow channel comprises a sample tank area, a flow channel detection area, and a waste liquid tank area, the sample tank area spatially corresponding to the sample loading area of the upper layer of the chip, the waste liquid tank area covering at least the slope structure or the groove of the lower layer of the chip, and the flow channel detection area being arc-shaped,
    the slope structure of the lower layer of the chip comprises a slope of 15° to 45°, and several cylindrical convex drainage points are distributed in the slope structure of the lower layer of the chip, or the groove spatially corresponds to a part of the waste liquid tank area and has a depth of 1 to 2 mm,
    the upper layer of the chip and the lower layer of the chip both have a thickness of 1.5 to 2.5 mm, and the intermediate layer of the chip has a thickness of 0.05 to 0.5 mm, and
    the sample loading area is provided with a slope structure that comprises a slope of 15° to 45°, and on which one or more cylindrical convex drainage points are distributed.

2. The microfluidic detection chip according to claim 1 wherein the lower layer of the chip further comprises a drainage groove spatially corresponding to the sample loading area.

3. The microfluidic detection chip according to claim 1, wherein a material for the upper layer of the chip and the lower layer of the chip is one selected from the group consisting of polystyrene, polydimethylsiloxane, polymethyl methacrylate, polyethylene terephthalate, glass and polycarbonate, and the intermediate layer of the chip is a polyethylene terephthalate adhesive or a polymethyl methacrylate adhesive.

4. A method of preparing the microfluidic detection chip according to claim 1, the method comprising:
    1) etching the sample flow channel in the double-sided adhesive layer by laser;
    2) tearing off a peeling layer on one side of the double-sided adhesive layer, and sticking the double-sided adhesive layer on the surface of the lower layer of the chip; and
    3) spotting the sample flow channel with a liquid, sticking the upper layer of the chip to the intermediate layer of the chip after drying the liquid, and pressing the upper layer of the chip.

5. A centrifugal detection device comprising:
    a microfluidic module, comprising the microfluidic detection chip according to claim 1;
    a fixing module, comprising a fixing device;
    a rotating module connected to the fixing device and configured to drive the fixing device to rotate; and
    a detection module configured to detect the flow channel detection area of the microfluidic detection chip through a light source transmitting area of the fixing device, and output a detection result,
    wherein the fixing device is configured to simultaneously fix a plurality of microfluidic detection chips according to claim 1, and comprises a central fixing disk and a rotating tray, the central fixing disk being positioned above the rotating tray, the rotating tray being divided by the central fixing disk into a plurality of areas each matching the microfluidic detection chip according to claim 1 in shape and each area comprising a side of the central fixing disk that fixes a microfluidic detection chip,
    wherein the light source transmitting area is concentric with the flow channel detection area of the microfluidic detection chip according to claim 1, and
    the central fixing disk is provided with positioning slots, which are evenly disposed on the sides of the central fixing disk.

* * * * *